US006875901B2

(12) United States Patent
Gartside et al.

(10) Patent No.: US 6,875,901 B2
(45) Date of Patent: Apr. 5, 2005

(54) OLEFIN ISOMERIZATION PROCESS

(75) Inventors: Robert J. Gartside, Summit, NJ (US); Marvin I. Greene, Wayne, NJ (US)

(73) Assignee: ABB Lummus Global Inc., Bloomfield, NJ (US)

( * ) Notice: Subject to any disclaimer, the term of this patent is extended or adjusted under 35 U.S.C. 154(b) by 144 days.

(21) Appl. No.: 09/863,973

(22) Filed: May 23, 2001

(65) Prior Publication Data

US 2003/0009072 A1 Jan. 9, 2003

(51) Int. Cl.[7] ............................. C07C 5/22; C07C 5/27; C07C 5/25
(52) U.S. Cl. ...................... 585/670; 585/667; 585/668; 585/664
(58) Field of Search ................................ 585/667, 668, 585/670, 664

(56) References Cited

U.S. PATENT DOCUMENTS

| 1,914,674 | A | 6/1933 | Runge |
| 3,169,987 | A | 2/1965 | Bloch |
| 4,217,244 | A | 8/1980 | Montgomery |
| 4,229,610 | A | 10/1980 | Myers et al. |
| 4,289,919 | A | 9/1981 | Myers |
| 4,575,575 | A | 3/1986 | Drake et al. |
| 4,754,098 | A | 6/1988 | Drake |
| 4,889,840 | A | 12/1989 | Drake |
| 5,087,780 | A | 2/1992 | Arganbright |
| 5,120,894 | A | 6/1992 | McCauley |
| 5,191,146 | A | 3/1993 | Gajda et al. |
| 5,292,985 | A | 3/1994 | Lattner et al. |
| 5,300,718 | A | 4/1994 | McCaulley |
| 5,304,696 | A | 4/1994 | Khare et al. |
| 5,336,831 | A | 8/1994 | Gajda et al. |
| 5,365,008 | A | 11/1994 | Barger et al. |
| 5,463,161 | A | 10/1995 | Gajda et al. |
| 5,489,726 | A | 2/1996 | Huss, Jr. et al. |
| 5,523,511 | A | 6/1996 | Haelsig et al. |
| 5,849,974 | A | 12/1998 | Clarembeau et al. |

FOREIGN PATENT DOCUMENTS

WO    WO 00/09261    2/2000

OTHER PUBLICATIONS

Lemberton et al., "Catalytic Isomerizastion of Ethylenic Hydrocarbons", Journal of Catalysis 89, pp. 69–78 (1984).
Baird et al., "Catalytic Sites for the Isomerizastion of 1–Butene Over Magnesium Oxide", Journal of Catalysis 26, pp. 440–450 (1972).
Hattori et al., "Catalytic Activities and Selectivities of Calcium and Magnesium Oxides for Isomerizastion of 1–Butene".

Primary Examiner—Thuan Dinh Dang
(74) Attorney, Agent, or Firm—Dilworth & Barrese, LLP

(57) ABSTRACT

An olefin isomerization process employs a basic metal oxide catalyst, such as magnesium oxide, which retains at least about 85 percent of its initial activity for at least about 168 hours of on-stream time. The catalyst is preferably a high purity magnesium oxide. The olefin isomerization process and catalyst described herein are advantageously used for the production of a terminal olefin such as 1-butene from an internal olefin such as 2-butene.

34 Claims, 6 Drawing Sheets under the nitrogen flow at 500° C. for approximately 2 hours. The temperature is then lowered to the reaction temperature under nitrogen flow.

OLEFIN ISOMERIZATION PROCESS

BACKGROUND OF THE INVENTION

1. Field of the Invention

The present invention relates to an olefin isomerization process employing a basic metal oxide catalyst and to the composition of the catalyst to improve its active life.

2. Description of the Related Art

There is a growing need for terminal (alpha) olefins such as 1-butene or 1-hexene. The commercial production of alpha olefins is usually accomplished by the isolation of the alpha olefin from a hydrocarbon stream containing a relatively high concentration of the 1-isomer. For example, 1-butene can be isolated from the $C_4$ product of steam cracking. Steam cracking $C_4$ streams contain not only the 1-butene stream but also 2-butene, isobutylene, butadiene and both normal and iso butanes. The 1-butene is isolated by first separating butadiene by extractive distillation or removing butadiene by hydrogenation. Isobutylene can be removed either by reaction (e.g. reaction with methanol to form MTBE), or by fractionation, with the remaining n-butenes being separated by distillation into a 1-butene overhead stream and a 2-butene bottom product. An alternate production method for alpha olefins involves the dimerization of ethylene to form 1-butene or the trimerization of ethylene to form 1-hexene. Other methods include molecular sieve adsorption of the linear olefins (used for low concentrations).

Another process for providing alpha olefins is catalytic isomerization from internal olefins, which accomplishes the shifting of the double bond in an olefin molecule from, for example, an internal position (2-butene) to a terminal position (1-butene). High temperatures favor the isomerization of internal olefin to the alpha olefin. However, high temperature tends to cause catalyst coking which shortens catalyst life. The duration of catalyst activity is a significant factor with respect to the economic viability of a process. The more often a process has to be interrupted for catalyst regeneration the more costly the process becomes. Hence, a method for maintaining peak catalyst activity over a longer period of time at high temperature is a significant advantage for olefin isomerization.

SUMMARY OF THE INVENTION

An olefin isomerization process is provided herein which comprises contacting a fluid feed stream containing an olefin with an activated basic metal oxide catalyst under olefin isomerization conditions, the activated catalyst having an initial activity for olefin isomerization and containing an amount of activity-affecting impurity which does not exceed that amount which will result in a reduction from the initial catalyst activity at a rate of 0.075 percent conversion loss/hr as measured by the isomerization conversion of 1-butene to 2-butene.

The invention herein advantageously provides a basic oxide isomerization catalyst possessing an extended period of catalyst activity at relatively high isomerization temperatures. The isomerization process is advantageously used for the isomerization of internal olefins such as 2-butene or 2-hexene to terminal olefins such as 1-butene or 1-hexene.

BRIEF DESCRIPTION OF THE DRAWINGS

Various embodiments of the invention are described herein with reference to the drawings wherein.

DETAILED DESCRIPTION OF PREFERRED EMBODIMENT(S)

The olefin isomerization method herein is directed to the conversion of internally olefinic compounds to terminally olefinic compounds. While the method is described below particularly with reference to the conversion of 2-butene to 1-butene, the conversion of any internally olefinic compound to the terminally olefinic isomer is encompassed within the scope of the invention. Thus, for example, the conversion of 2-pentene to 1-pentene, 2-hexene or 3-hexene to 1-hexene, 2-heptene or 3-heptene to 1-heptene, and the like are also contemplated.

In a typical olefins plant, saturated hydrocarbons are converted to a mixture of olefins by a cracking process such as thermal cracking, steam cracking, fluid catalytic cracking and the like.

The resultant effluent from that cracking reaction is separated into carbon number fractions using a series of distillation columns and refrigerated heat exchange. In one sequence, a demethanizer is used for the removal of methane and hydrogen followed by a deethanizer for the removal of ethane, ethylene, and $C_2$ acetylene. The bottoms from this deethanizer tower consist of a mixture of compounds ranging in carbon number from $C_3$ to $C_6$. This mixture is separated into different carbon numbers, typically by fractionation.

The $C_3$ cut, primarily propylene, is removed as product and is ultimately used for the production of polypropylene or as a feedstock for synthesis of cumene or propylene oxide or acrylonitrile or other important chemical intermediates. The methyl acetylene and propadiene (MAPD) impurities must be removed either by fractionation or hydrogenation. Hydrogenation is preferred since some of these highly unsaturated $C_3$ compounds end up as propylene thereby increasing the yield.

The $C_4$ cut consisting of $C_4$ acetylenes, butadiene, iso and normal butenes, and iso and normal butane can be processed in many ways. A typical steam cracker $C_4$ cut contains components as set forth in Table 1. Table 1 is given for purposes of exemplification only. Component percentages of $C_4$ streams can be outside of the ranges given in Table 1.

TABLE 1

| | |
|---|---|
| $C_4$ acetylenes | trace |
| butadiene | 30–40 wt. percent |
| 1-butene | 10–20 wt. percent |
| 2-butene | 5–15 wt. percent |
| isobutene | 20–40 wt. percent |
| iso & normal butane | 5–15 wt. percent |

Figure 1:
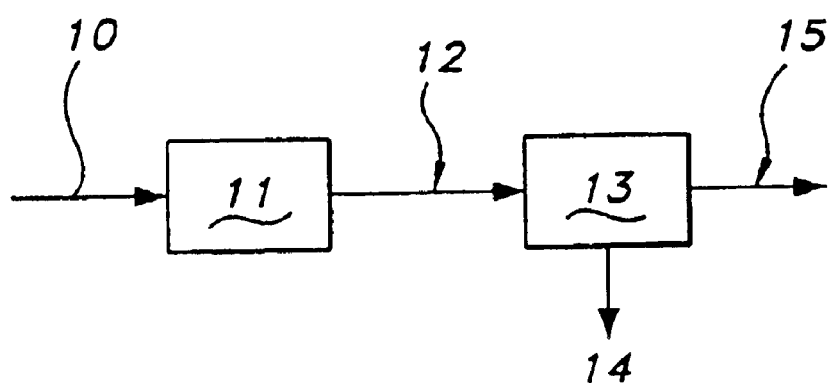
FIG. 1 is a schematic flow diagram of a method for treating a mixture of $C_4$ compounds from a cracker.

In a preferred method the processing of the $C_4$ stream is diagrammatically illustrated in FIG. 1. A stream 10 containing a mixture of $C_4$ components is sent to a catalytic distillation/hydrogenation unit 11 for hydrogenating the $C_4$-acetylenes and the butadiene to 1-butene and 2-butene. Hydrogenation can be performed in a conventional manner in a fixed bed or alternately in a catalytic distillation unit. The catalytic hydrogenation unit 11 can employ any suitable hydrogenation catalyst such as, for example, palladium on alumina, in a packed bed. Hydrogen can be added at a level representing 1.0 to 1.5 times the hydrogen required to hydrogenate the dienes and acetylenes to olefins. The conditions are variable depending on reactor design. If, for example, the catalytic hydrogenation unit 11 is operated as a catalytic distillation unit, the temperature and pressure are consistent with fractionation conditions. The $C_4$ fraction 12 produced by catalytic hydrogenation unit 11 contains mainly 1-butene, 2-butene, isobutene and a small amount of other components such as normal and iso butanes.

Under such conditions of hydrogenation, hydroisomerization reactions also occur. Significant quantities of 2-butene are formed by the hydroisomerization of 1-butene, which is produced by the hydrogenation of butadiene.

The fraction 12, now containing only olefins and paraffins, is processed for the removal of the isobutylene fraction in unit 13. There are a number of processes that will accomplish this.

In a preferred method the isobutene is removed by catalytic distillation combining hydroisomerization and super-fractionation in unit 13. The hydroisomerization converts 1-butene to 2-butene, and the superfractionation removes the isobutene in stream 14, leaving a relatively pure 2-butene stream 15 containing some n-butane. The advantage to converting the 1-butene to 2-butene in this system is that the boiling point of 2-butene (1° C. for the trans isomer, 4° C. for the cis isomer, 4) is further away from the boiling point of isobutylene (−7° C.) than that of 1-butene (−6° C.), thereby rendering the removal of isobutene by superfractionation easier and less costly and avoiding the loss of 1-butene overhead with the isobutylene. The relatively pure 2-butene stream 15 is used as a feed steam F for the olefin isomerization process described below.

Alternately, unit 13 (isobutylene removal) could be an MTBE unit where isobutylene is removed via reaction with methanol to form MTBE. The remaining normal olefins (stream 15) consisting of 1 and 2-butenes, are relatively untouched in this reaction.

Figure 2:
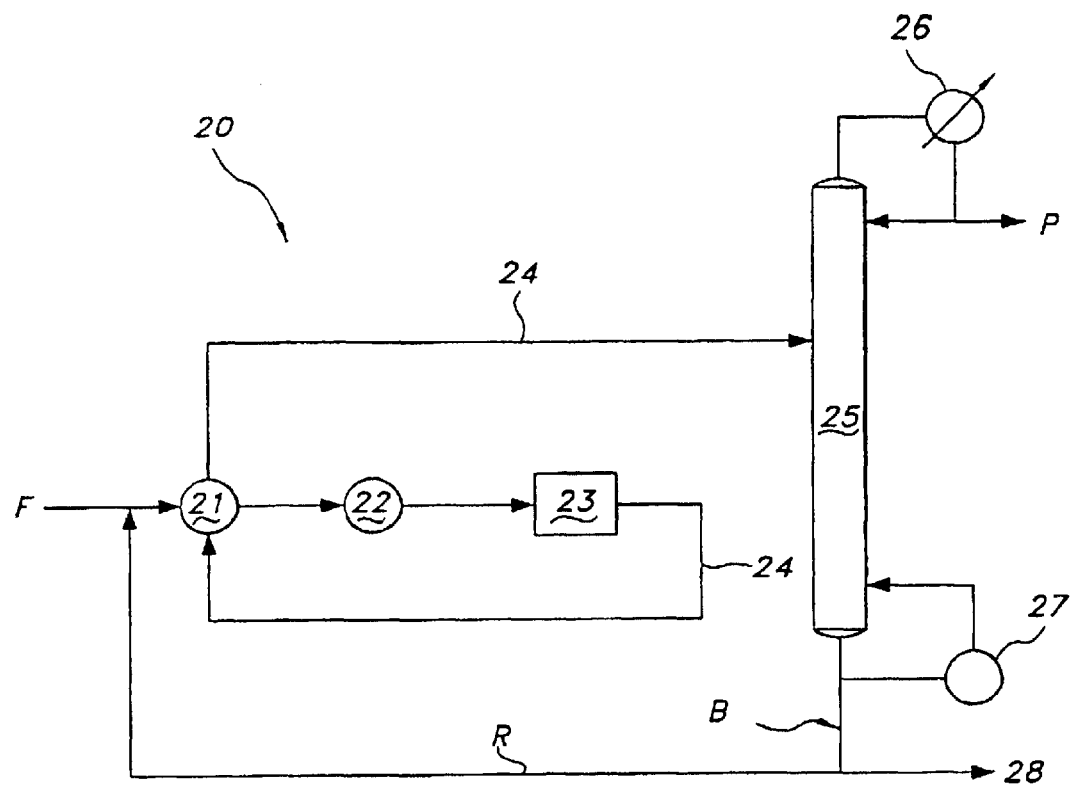
FIG. 2 is a schematic flow diagram of the olefin isomerization process of the present invention.

Referring now to FIG. 2, the isomerization of a feed F containing primarily 2-butene by the system 20 is illustrated. Feed F is mixed with a 2-butene recycle stream R and is sent to a first heat exchanger 21 wherein heat is recovered from the effluent stream 24 of the isomerization reactor 23. Feed F is then sent to a heater 22 which raises the temperature of the feed stream to a preferred isomerization temperature of at least about 250° C., preferably from about 300° C. to about 600° C., more preferably from about 340C to about 500° C. Feed F then enters isomerization reactor 23 where it is contacted with an isomerization catalyst, such as described below, at the isomerization temperature. Reaction pressure is not critically important and can range from subatmospheric to more than 400 psig. Reactor 23 can be any reactor suitable for isomerization such as axial flow, radial flow or parallel flow. The catalyst can be in the form of particulate such as powder, pellets, extrudate, etc.

As stated above, higher temperatures shift the reaction equilibrium to favor the production of 1-butene. At the isomerization temperatures indicated above, a 2-butene conversion of 20 percent to 30 percent to 1-butene is achievable.

The effluent 24 is passed through heat exchanger 21, for heat recovery and is then sent to a fractionator 25 for separation of the 1-butene and 2-butene isomers. Condenser 26 recycles 1-butene for reflux. A relatively pure 1-butene stream is drawn off as overhead product P. A bottoms fraction B containing unreacted 2-butene and butanes is produced. A portion of the 2-butene rich bottoms is sent via recycle stream R back to the feed F. A small portion of the bottoms fraction is bled off at stream 28. Since the feed F contains some butanes, which are unreacted and are separated with the fractionator bottoms, the butanes would accumulate through recycling, thereby wasting energy if the bottoms were not bled. One skilled in the art would adjust the amount of bottoms bled off stream 28 and recycled via stream R to achieve the most economical operation of the system 20.

Useful isomerization catalysts include basic metal oxides such as magnesium oxide, calcium oxide, barium oxide, and lithium oxide, either individually or in combination. Other oxides such as sodium oxide or potassium oxide can be incorporated into the catalyst as promoters. The preferred catalyst for use in the isomerization method described herein is magnesium oxide (MgO) and the invention will be described in terms of magnesium oxide, although it should be understood that the other basic metal oxides mentioned above are also contemplated as being within the scope of the invention. The magnesium oxide catalyst can be in the form of powder, pellets, extrudates, and the like.

One of the problems associated with magnesium oxide and other basic oxide catalysts is the shortness of the duration of its catalytic activity under favorable isomerization conditions of high temperature to form the alpha olefin. Conventional magnesium oxide (or other basic metal oxide) catalyst experiences a rapid drop of catalyst activity after about 20–40 hours of operation on-stream. The deactivation rates as measured by the loss of conversion of 1-butene to 2-butene are approximately 0.3 percent conversion loss/hr or higher. Such a rapid loss from the initial activity either as a fresh catalyst or regenerated catalyst renders the process economically less feasible and inhibits the wider use of magnesium oxide as an isomerization catalyst.

Typically, the catalyst is treated in dry inert gas to remove residual water and carbon dioxide prior to use in the isomerization reaction. Water and carbon dioxide are generally chemically bound to the magnesium oxide in the form of magnesium hydroxide and magnesium carbonate. Although not wishing to be bound by any explanation, it is believed that these compounds act as acid sites which promote the fouling reactions that limit the onstream cycle life of the system.

A significant feature of the basic oxide catalyst used in the present method is its purity. Certain impurities adversely affect the activity of the basic metal oxide catalyst. Activity-affecting impurities such as sulfur or phosphorous (usually in the form of compounds such as sulfides, sulfates, phosphates, and the like) can form highly acidic oxides which lead to undesirable cracking reactions which foul the catalyst and limit the cycle life at desirable isomerization conditions. Likewise, activity-affecting impurities such as transition metal (e.g., iron, chromium, cobalt and nickel in their oxide form) are believed to act as catalysts for various cracking and dehydrogenation reactions which lead to coke formation and also limit the cycle life of the catalyst and desirable isomerization conditions. The amount of activity-affecting impurity should be as small as possible. Preferably, the amount of activity-affecting impurity in the catalyst does not exceed that amount which would result in a reduction of catalyst activity at a rate of not more than about 0.075 percent conversation loss/hr as measured by the isomerization of 1-butene to 2-butene, the catalyst preferably having not more than about 0.050 percent conversion loss/hr, and more preferably not more than about 0.035 percent conversion loss/hr. The 0.075% conversion loss/hr translates into an equivalent of a 1 week cycle length defined by an approximate 15 percent loss in 1-butene conversion over the time period.

Accordingly, the basic metal oxide catalyst of the present invention contains, in parts by weight, no more than about 2000 ppm of sulfur and/or phosphorous, and no more than about 500 ppm of transition metal, preferably no more than about 1000 ppm of sulfur and/or phosphorous and no more than about 400 ppm of transition metal, and most preferably no more than about 75 ppm of sulfur and/or phosphorous and no more than about 330 ppm of transition metals.

While the adverse affect on catalyst life caused by water and carbon dioxide can be reversed under activation or regeneration temperatures, the acid sites caused by sulfur, phosphorous, or transition metals are not easily removed. Accordingly, it is important that the basic metal oxide initially be of high purity. High purity basic metal oxides can be prepared by one skilled in the art or can be obtained commercially.

Table 2 below sets forth a comparison of the impurity levels of a preferred high purity magnesium oxide catalyst and a conventional magnesium oxide catalyst.

TABLE 2

| Impurity | High purity MgO Impurity level (ppm) | Conventional grade MgO Impurity level (ppm) |
| --- | --- | --- |
| Iron | 330 | 692 |
| Sulfur | 74 | 2335 |
| Calcium | 4100 | 3522 |
| Sodium | 2250 | 2250 |

Prior to its initial use in an olefin isomerization reaction the magnesium oxide (or other basic metal oxide catalyst) is heated in a dry inert atmosphere at sufficiently high temperature to remove substantially all activity-affecting amounts of water and carbon dioxide. A suitable initial activation treatment of the magnesium oxide catalyst can be performed in one or more steps. Preferably, a two step process is employed wherein the magnesium oxide catalyst is first preheated for at least about 15 hours at a temperature of least 350° C. in a dry inert atmosphere as a drying first step. More particularly, a flow of dry pure inert gas such as nitrogen is passed through a bed of magnesium oxide catalyst at a temperature of at least about 350° C. for at least about 15 hours while the effluent is monitored for release of water and carbon dioxide. The effluent water concentration is brought down to less than 1 ppm.

In a preferred second step the catalyst is activated by contact with an inert gas (e.g., nitrogen) at about at least 500° C., preferably at about at least 550° C. for at least about 6 hours. This removes even more $CO_2$ and $H_2O$.

While the initial treatment method described above improves the catalyst performance enabling operation of the isomerization for a period of over 150 hours, the olefin isomerization process must be cycled to allow for regeneration of the catalyst to remove coke deposits. The benefit of the dry-out achieved by the treatment method set forth above is lost on the second cycle when standard regeneration procedures are employed.

The regeneration method herein restores the catalyst to substantially its initial fresh condition and includes a decoking step, preferably followed by a high temperature catalyst reactivation step.

The decoking step substantially completely removes all activity affecting amounts of coke. In the decoking process however, water and carbon dioxide, which are both products of combustion, are deposited on the catalyst surface. The high temperature reactivation step removes substantially any remaining traces of water and/or carbon dioxide capable of affecting catalyst activity for further extension of catalyst life and restores the catalyst to substantially its initial level of activity. More particularly, the decoking step includes contacting the catalyst with a flowing atmosphere containing a dry inert gas (e.g., nitrogen) and an oxidizing agent (e.g., oxygen) at a final regeneration temperature of at least about 500° C. for at least about 18 hours to substantially completely remove all coke from the catalyst. The regeneration proceeds in steps of gradually increasing temperature and oxygen concentration as described in U.S. Pat. No. 4,217,244, which is herein incorporated by reference. In the final step, the catalyst is exposed to high levels of oxygen. Pure, dry air with at least about 20 volume percent oxygen is preferably used as the flowing atmosphere. Following the oxidation step, the catalyst is exposed to the procedure for reactivation as used prior to initial operation. A two step nitrogen dryout to remove the products of combustion is utilized.

A preferred activation method for the olefin isomerization catalyst is disclosed and described in U.S. patent application Ser. No. 09/863,974 filed concurrently herewith, which is herein incorporated by reference.

Various aspects of the invention are illustrated by the Examples and Comparative Examples given below:

EXAMPLE 1

A sample of high purity magnesium oxide (hereinafter designated as Sample A) was provided, the sample containing 330 ppm iron, 74 ppm sulfur, 4100 ppm calcium and less than 250 ppm sodium.

Sample A was treated according to the initial dryout procedures referenced above. Sample A was then operated in 1-butene isomerization conditions and was coked until substantially all catalyst activity was lost. After a nitrogen flush, the sample was exposed to a regeneration procedure consisting of a programmed increase in temperature and oxygen concentration with a final step of exposure to nitrogen containing 21 percent oxygen for 18 hours at 500° C. Thereafter, a high temperature reactivation step was performed on the sample by exposing the sample to dry nitrogen at 550° C. The sample was treated with nitrogen containing approximately 10 ppm of oxygen.

Sample A was then individually tested in an isomerization of 1-butene to 2-butene for catalyst activity. The isomerization reaction was conducted at 450 psig, 515° F. and 27 WHSV. The feed stream included 65 percent diluent. The catalyst activity was measured in terms of the 1-butene conversion in mol percent.

Figure 3:
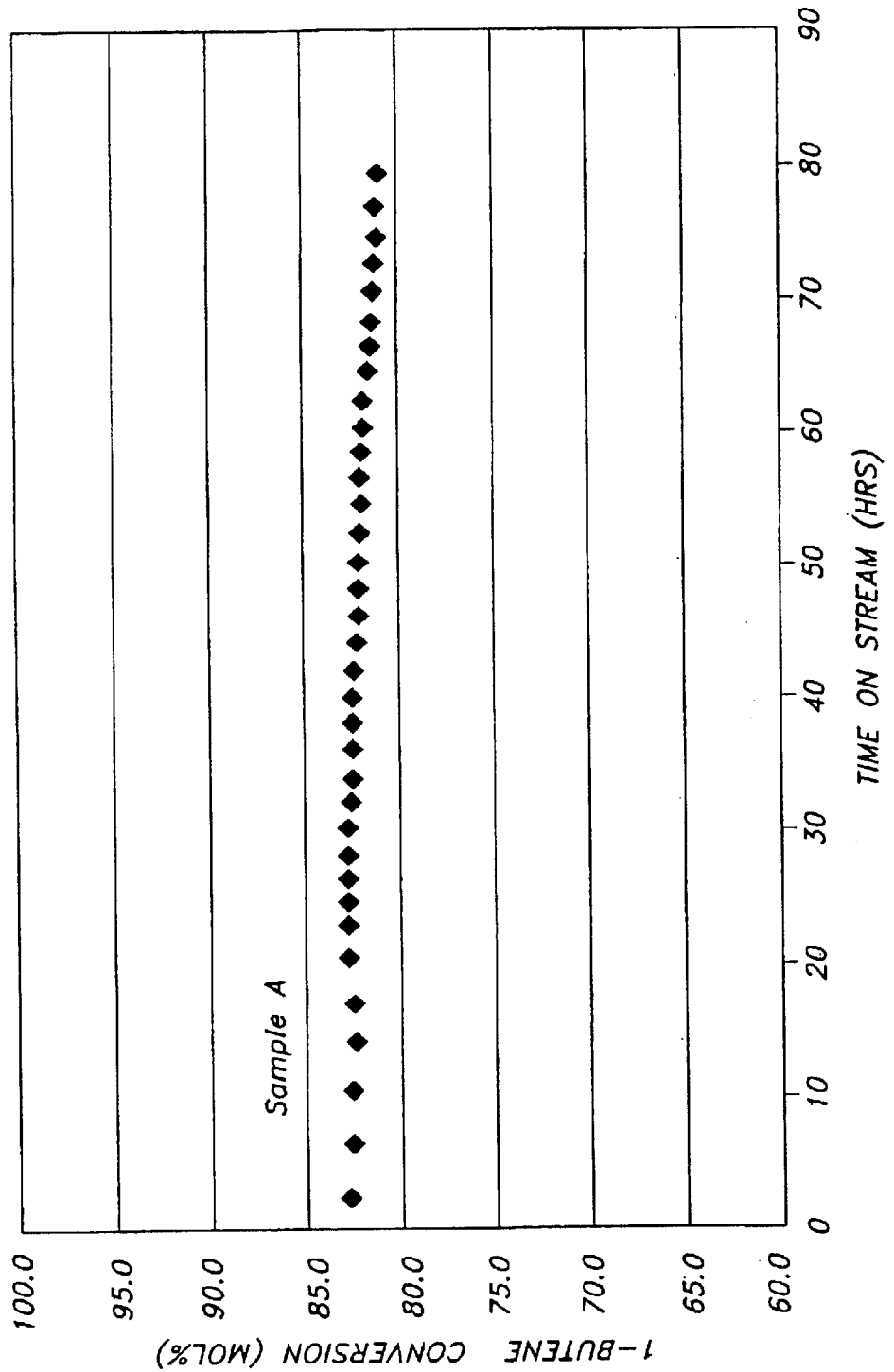
FIGS. 3 and 4 are charts illustrating the 1-butene olefin isomerization conversion vs. time achieved by magnesium oxide catalyst of the present invention; and, FIGS. 5 and 6 are charts illustrating the 1-butene olefin isomerization conversion vs. time achieved by conventional magnesium oxide catalyst.

The results of this test are tabulated in Table 3 and graphically illustrated in FIG. 3. As can be seen the overall deactivation rate of Sample A was 0.033 percent conversion lost per hour.

EXAMPLE 2

A sample of high purity magnesium oxide (hereinafter designated as Sample B) was provided, the sample containing 330 ppm iron, 74 ppm sulfur, 4100 ppm calcium and less than 250 ppm sodium.

Sample B was treated according to the same procedures as set forth above in Example 1.

Sample B was then individually tested in an isomerization of 1-butene for catalyst activity. The isomerization reaction was conducted at 450 psig, 520° F. and 26.6 WHSV. The feed stream included 65 percent diluent. The catalyst activity was measured in terms of the 1-butene conversion in mol percent.

Figure 4:
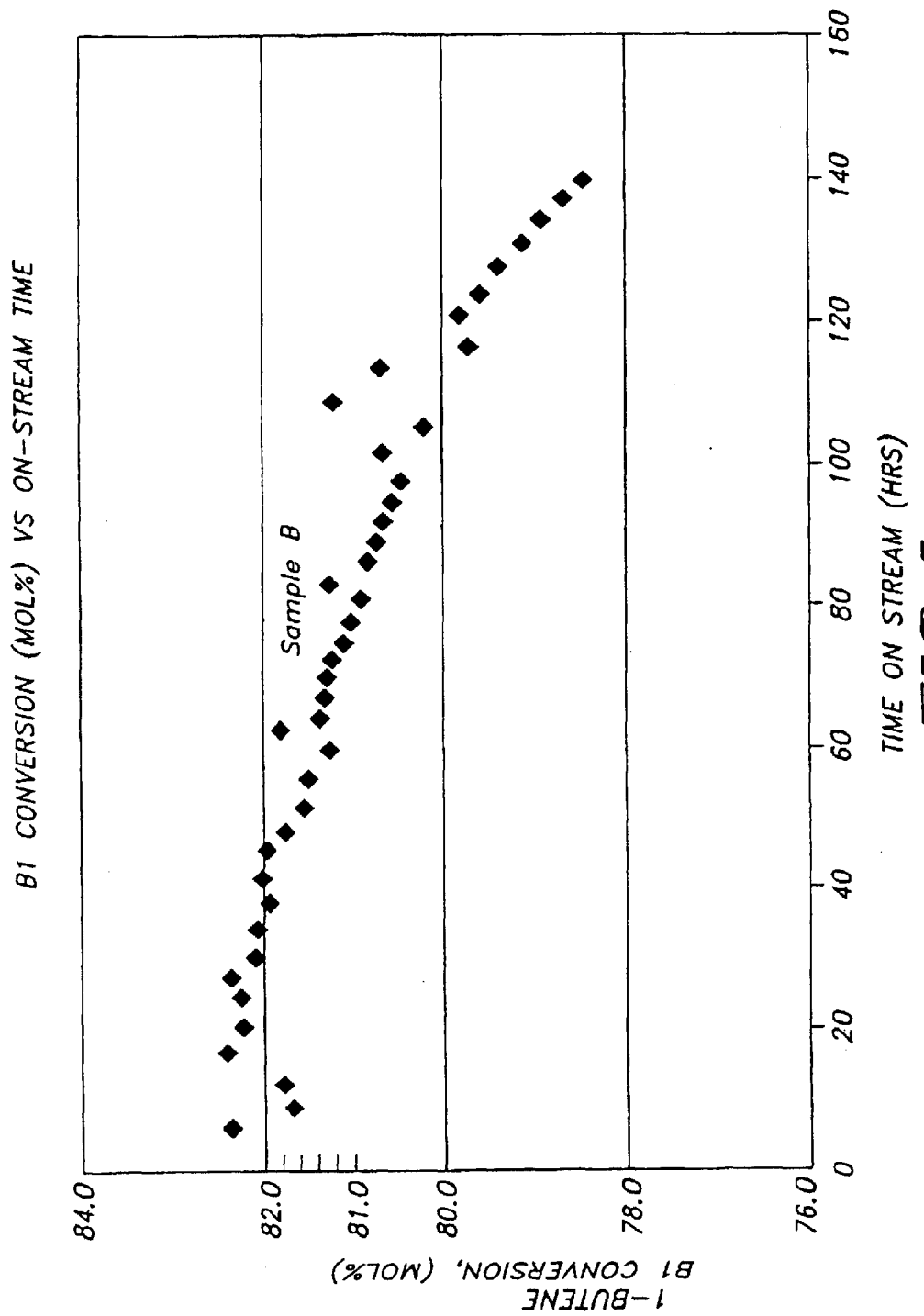

The results of this test are tabulated in Table 3 and graphically illustrated in FIG. 4. As can be seen the overall deactivation rate of Sample B was 0.027 percent conversion lost per hour.

Comparative Example 1

A sample of conventional grade magnesium oxide (hereinafter designated as Sample C) was provided, the sample containing 692 ppm iron, 2335 ppm sulfur, 3522 ppm calcium and less than 250 ppm sodium.

Sample C was treated according to the same procedures as set forth above in Example 1.

Sample C was then individually tested in an isomerization of 1-butene for catalyst activity. The isomerization reaction was conducted at 450 psig, 519° F. and 27 WHSV. The feed stream included 65 percent diluent. The catalyst activity was measured in terms of the 1-butene conversion in mol percent.

Figure 5:
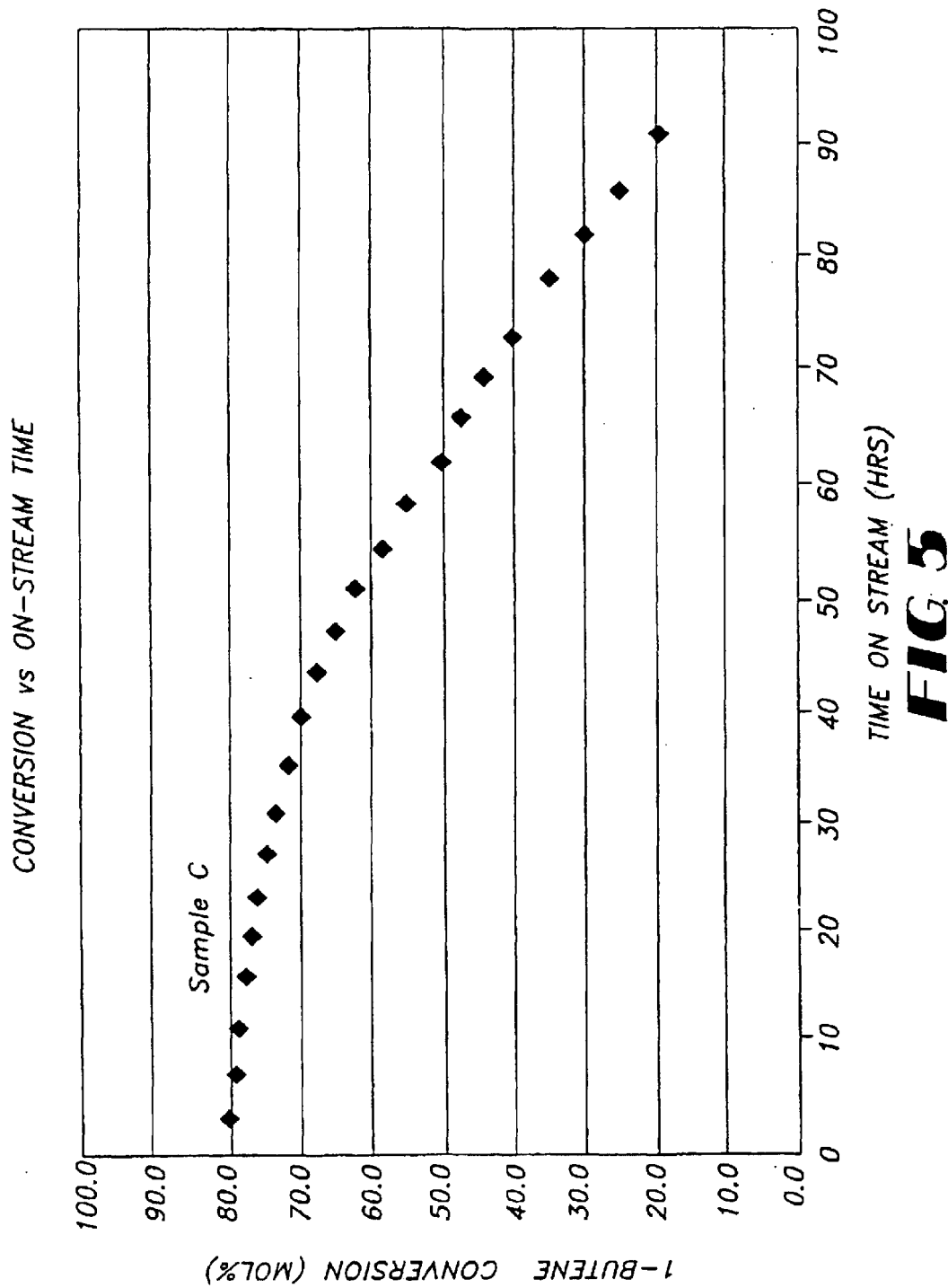

The results of this test are tabulated in Table 3 and graphically illustrated in FIG. 5. As can be seen the overall deactivation rate of Sample C was 0.281 percent conversion lost per hour.

Comparative Example 2

A sample of conventional grade magnesium oxide (hereinafter designated as Sample D) was provided, the sample containing 692 ppm iron, 2335 ppm sulfur, 3522 ppm calcium and less than 250 ppm sodium.

Sample D was treated according to the same procedures as set forth above in Example 1.

Sample D was then individually tested in an isomerization of 1-butene for catalyst activity. The isomerization reaction was conducted at 76 psig, 517° F. and 9 WHSV. The feed stream included 65 percent diluent. The catalyst activity was measured in terms of the 1-butene conversion in mol percent.

Figure 6:
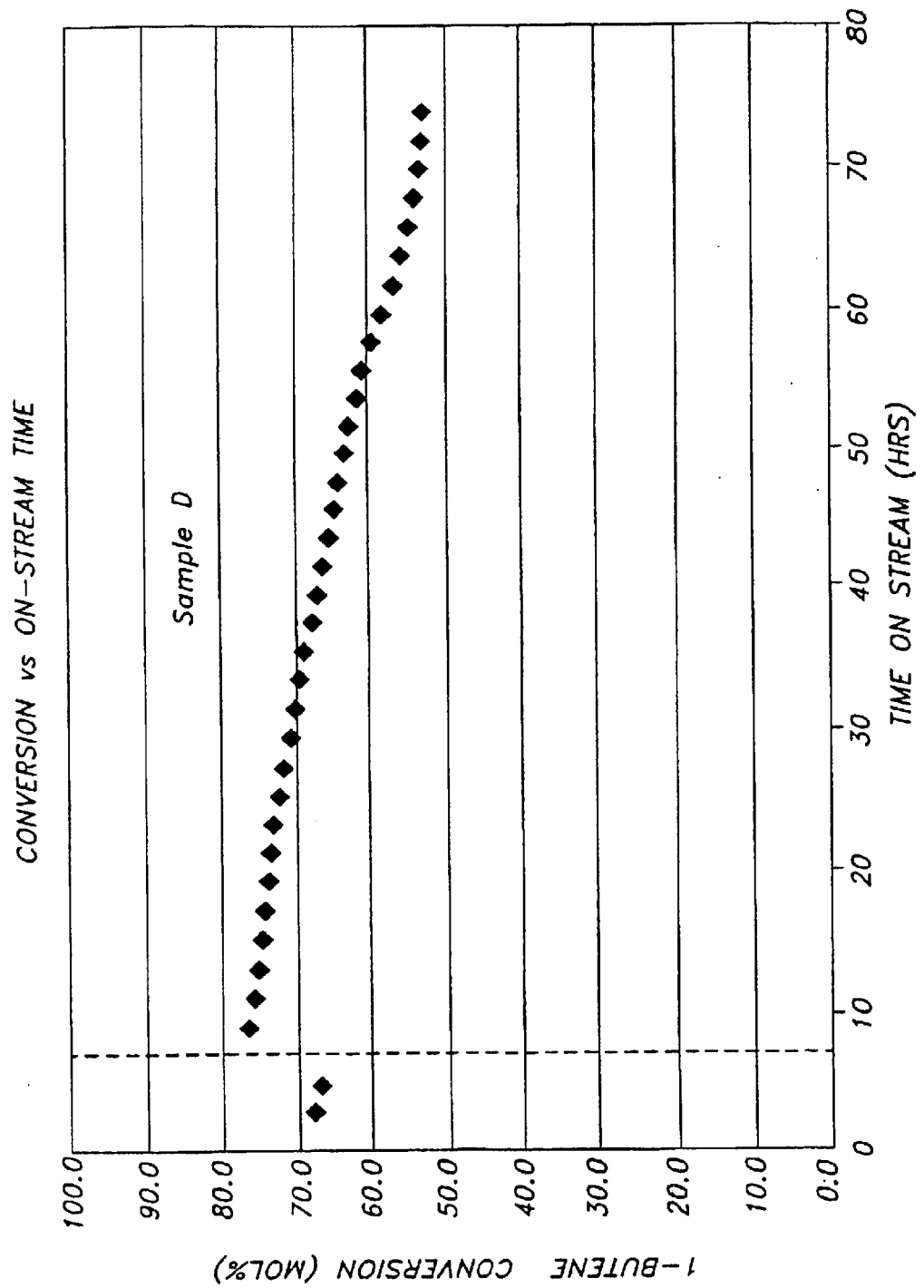

The results of this test are tabulated in Table 3 and graphically illustrated in FIG. 6. As can be seen the overall deactivation rate of Sample D was 0.373 percent conversion lost per hour. Increasing the amount of catalyst by a factor of 3 (i.e., a WHSV of 9 as opposed to a WHSV of 27) did not materially change the rate of conversion loss for the entire system.

These results show that conventional grade magnesium oxide olefin catalysts experience a loss of olefin conversion activity which is about 10 times greater than the high purity magnesium oxide catalysts of the present invention under desirable olefin isomerization conditions. Moreover, the high purity catalyst exhibited a higher initial conversion to 2-butene.

TABLE 3

| Sample | A-High Purity MgO | B-High Purity MgO | C-Commercial MgO | D-Commercial MgO |
|---|---|---|---|---|
| Initial 1-$C_4$ Conversion, mol % | 83.1 | 82.4 | 80.4 | 77.0 |
| Final 1-$C_4$ Conversion mol %/hours | 80.5%/80 | 78.0%/148 | 70.0/40 | 53.5/72 |
| Deactivation Rate % lost/hr | 0.033 | 0.027 | 0.281 | 0.373 |
| Pressure | 450 psig | 450 psig | 450 psig | 76 psig |
| Temperature | 515° F. | 520° F. | 519° F. | 517° F. |
| WHSV, lb/lb/hr | 27 | 26.6 | 27 | 9 |

It will be understood that various modifications may be made to the embodiments described herein. Therefore, while the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. An olefin double bond isomerization process which comprises contacting a fluid feed stream containing an olefin with an activated basic metal oxide catalyst under olefin isomerization conditions, the activated catalyst having an initial activity for olefin isomerization and containing an amount of activity-affecting impurity which does not exceed that amount which will result in a reduction of catalyst activity by about 0.075 percent conversion loss per hour as measured by the isomerization of 1-butene to 2-butene under the isomerization conditions wherein the activity-affecting impurity in the basic metal oxide catalyst is, or contains, sulfur, phosphorus, at least one transition metal or combination thereof.

2. The olefin isomerization process of claim 1 wherein the basic metal oxide catalyst is selected from the group consisting of magnesium oxide, calcium oxide, barium oxide, lithium oxide and combinations thereof.

3. The olefin isomerization process of claim 1 wherein the catalyst is magnesium oxide.

4. The olefin isomerization process of claim 1 wherein the at least one transition metal is iron, chromium, cobalt, nickel, or a combination thereof.

5. The olefin isomerization process of claim 1 wherein the catalyst contains no more than about 2000 ppm of sulfur and/or phosphorous and no more than about 500 ppm of one or more transition metals.

6. The olefin isomerization process of claim 1 wherein the catalyst contains no more than about 1000 ppm of sulfur and/or phosphorous and no more than about 400 ppm of one or more transition metals.

7. The olefin isomerization process of claim 1 wherein the catalyst contains no more than about 75 ppm of sulfur and/or phosphorous and no more than about 330 ppm of one or more transition metals.

8. The olefin isomerization process of claim 1 wherein the fluid feed stream comprises an olefin possessing an internal double bond, at least some of the olefin possessing an internal double bond being converted to a corresponding terminal olefin.

9. The olefin isomerization process of claim 8 wherein the olefin possessing an internal double bond comprises 2-hexene and/or 3-hexene and the corresponding terminal olefin is 1-hexene.

10. The olefin isomerization process of claim 8 wherein the olefin possessing an internal double bond is 2-butene and the corresponding terminal olefin is 1-butene.

11. The olefin isomerization process of claim 10 wherein the conversion of 2-butene to 1-butene is from about 20 percent to about 30 percent.

12. The olefin isomerization process of claim 1 wherein the olefin isomerization conditions include a temperature of at least about 300° C.

13. The olefin isomerization process of claim 1 wherein the olefin isomerization conditions include a temperature of from about 340° C. to about 500° C.

14. The olefin isomerization process of claim 1 wherein the basic metal oxide catalyst is selected from the group consisting of magnesium oxide, calcium oxide, barium oxide, lithium oxide and combinations thereof, and the activity-affecting impurity includes sulfur, phosphorus at least one transition metal or a combination thereof.

15. The olefin isomerization process claim 14 wherein the at least one transition metal is iron, chromium, cobalt, nickel, or a combination thereof.

16. The olefin isomerization process of claim 3 wherein the catalyst contains no more than about 2000 ppm of sulfur and/or phosphorous and no more than about 500 ppm of one or more transition metals.

17. The olefin isomerization process of claim 3 wherein the catalyst contains no more than about 1000 ppm of sulfur and/or phosphorous and no more than about 400 ppm of one or more transition metals.

18. The olefin isomerization process of claim 3 wherein the catalyst contains no more than about 75 ppm of sulfur and/or phosphorous and no more than about 330 ppm of one or more transition metals.

19. A process for isomerizing $C_4$ olefin derived from a mixed $C_4$ stream comprising the steps of:
  a) providing a $C_4$ feed stream containing butadiene, 1-butene, 2-butene, and isobutylene;
  b) selectively hydrogenating the $C_4$ feed stream in the presence of a hydrogenation catalyst and hydrogen whereby the butadiene is selectively hydrogenated to provide a first intermediate $C_4$ stream containing 1-butene, 2-butene, and isobutylene;
  c) simultaneously hydroisomerizing and fractionating the first intermediate $C_4$ stream to convert 1-butene to 2-butene and to remove the isobutylene by fractionation to produce a second intermediate $C_4$ stream containing a higher concentration of 2-butene than in the $C_4$ feed stream; and
  d) contacting the second intermediate $C_4$ stream with an activated basic metal oxide catalyst under olefin isomerization conditions, the activated catalyst having an initial activity for olefin isomerization and containing an amount of activity-affecting impurity which does not exceed that amount which will result in a reduction of catalyst activity by about 0.075 percent conversion loss per hour as measured by the isomerization of 1-butene to 2-butene under the isomerization conditions, wherein the activity-affecting impurity in the basic metal oxide catalyst is, or contains, sulfur, phosphorus, at least one transition metal or combination thereof.

20. The process of claim 19 wherein the basic metal oxide catalyst contains no more than about 2000 ppm of sulfur and/or phosphorous and no more than about 500 ppm of one or more transition metals.

21. The process of claim 19 wherein the basic metal oxide catalyst contains no more than about 1000 ppm of sulfur and/or phosphorous and no more than about 400 ppm of one or more transition metals.

22. The process of claim 19 wherein the basic metal oxide catalyst contains no more than about 75 ppm of sulfur and/or phosphorous and no more than about 330 ppm of one or more transition metals.

23. An olefin isomerization process which comprises contacting a fluid feed stream containing an olefin under olefin isomerization conditions with an activated catalyst consisting essentially of a basic metal oxide, the activated catalyst containing no amount of activity-affecting impurity which results in a deactivation rate of catalyst isomerization activity exceeding about 0.075 percent conversion loss per hour as measured by the isomerization of 1-butene to 2-butene under the isomerization conditions, wherein the activity-affecting impurity in the basic metal oxide catalyst is, or contains, sulfur, phosphorus, at least one transition metal or combination thereof.

24. The olefin isomerization process of claim 23 wherein the basic metal oxide is selected from the group consisting of magnesium oxide, calcium oxide, barium oxide, lithium oxide and combinations thereof.

25. The olefin isomerization process of claim 23 wherein the basic metal oxide is magnesium oxide.

26. The olefin isomerization process of claim 24 wherein the transition metal is iron, cobalt, nickel, or a combination thereof.

27. The olefin isomerization process of claim 24 wherein the catalyst contains no more than about 2000 ppm of sulfur and/or phosphorous and no more than about 500 ppm of one or more transition metals.

28. The olefin isomerization process of claim 24 wherein the catalyst contains no more than about 1000 ppm of sulfur and/or phosphorous and no more than about 400 ppm of one or more transition metals.

29. The olefin isomerization process of claim 24 wherein the catalyst contains no more than about 75 ppm of sulfur and/or phosphorous and no more than about 330 ppm of one or more transition metals.

30. The olefin isomerization process of claim 24 wherein the fluid feed stream comprises an olefin processing an internal double bond, at least some of the olefin possessing an internal double bond being converted to a corresponding terminal olefin.

31. The olefin isomerization process of claim 30 wherein the olefin possessing an internal double bond comprises 2-hexene and/or 3-hexene and the corresponding terminal olefin is 1-hexene.

32. The olefin isomerization process of claim 30 wherein the olefin possessing an internal double bond is 2-butene and the corresponding terminal olefin is 1-butene.

33. The olefin isomerization process of claim 23 wherein the deactivation rate of catalyst activity does not exceed 0.033 mol. % conversion loss per hour.

34. The olefin isomerization process of claim 23 wherein the deactivation rate of catalyst activity does not exceed 0.027 mol. % conversion loss per hour.

* * * * *